US007157155B2

(12) United States Patent
Che et al.

(10) Patent No.: US 7,157,155 B2
(45) Date of Patent: Jan. 2, 2007

(54) MATERIALS FOR ELECTROLUMINESCENT DEVICES

(75) Inventors: Chi-Ming Che, Hong Kong (CN); Iona Hiu Tung Sham, Chai Wai (HK)

(73) Assignee: The University of Hong Kong, Hong Kong (HK)

( * ) Notice: Subject to any disclaimer, the term of this patent is extended or adjusted under 35 U.S.C. 154(b) by 362 days.

(21) Appl. No.: 10/753,528

(22) Filed: Jan. 9, 2004

(65) Prior Publication Data
US 2005/0153164 A1 Jul. 14, 2005

(51) Int. Cl.
H01L 51/54 (2006.01)
H05B 33/12 (2006.01)
(52) U.S. Cl. ............... 428/690; 428/704; 428/917; 313/504; 313/506; 257/40; 257/E51.047
(58) Field of Classification Search ............ 564/9, 564/10; 568/3
See application file for complete search history.

(56) References Cited

U.S. PATENT DOCUMENTS

| 3,166,520 | A | * | 1/1965 | English et al. | |
| 3,172,862 | A | | 3/1965 | Gumee et al. | |
| 4,356,429 | A | | 10/1982 | Tang | 313/503 |
| 5,061,569 | A | | 10/1991 | VanSlyke et al. | 428/457 |
| 5,247,190 | A | | 9/1993 | Friend et al. | 257/40 |
| 5,292,830 | A | * | 3/1994 | Funayama et al. | 525/478 |
| 6,458,719 | B1 | | 10/2002 | Tsunoda et al. | 438/778 |
| 2002/0057046 | A1 | * | 5/2002 | Yamamoto et al. | 313/311 |
| 2005/0230665 | A1 | * | 10/2005 | Thompson | 252/500 |

FOREIGN PATENT DOCUMENTS

| GB | 1050434 | 12/1966 |
| WO | WO 90/13148 A1 | 11/1990 |

OTHER PUBLICATIONS

"Hole Transporting Materials with High Glass Transition Temperatures for Use in Organic Light-Emitting Devices"; O'Brien, et al.; *Adv. Mater.*; 1998, 10, No. 14 pp. 1108-1112.
"Recent progress of molecular organic electroluminescent materials and devices"; Hung, et al.; *Materials Science and Engineering*; R 39 (2002) 143-222.
"Improved Time-of-Flight Technique for Measuring Carrier Mobility in Thin Films of Organic Electroluminescent Materials"; Chen, et al.; *Jpn. J. Appl. Phys.*; Part1, vol. 39, No. 3A, (2000), pp. 1190-1192.
"Improved Red Dopants For Organic Electroluminescent Devices"; Chen, et al.; *Marcromol. Symp.*; 125, 49-58 (1997).
"Organoboron Compounds. I. A New Synthesis of B-Trialkyl and Triaryl-N-triphenylborazoles"; Groszos, et al.; *J. Am. Chem. Soc.*; 81, Mar. 20, 1958, pp. 1357-1360.
"Boron-Nitrogen Compounds. I. Synthesis of B-Aminoborazines"; Niedenzu, et al.; *J. Am. Chem. Soc.*; 81, Jul. 20, 1959, 3561-3564.
"Convenient Preparation of B-Trichloroborazine"; Rothgery, et al.; *Inorganic Chemistry*; vol. 6, No. 5, May 1967, pp. 1065-1066.
"Electron and hole mobility in tris(8-hydroxyquinolinato-N1,O8) aluminum"; Kepler, et al.; *Appl. Phys. Lett.*; 66 (26), Jun. 26, 1995, pp. 3618-3620.
"Improved Luminous Efficiency of Organic Light-Emitting Diodes by Carrier Trapping Dopants"; Hamada et al.; *Jpn. J. Appl. Phys.*; vol. 40 (2001), pp. L753-L755.
"Electron drift mobility and electroluminescent efficiency of tris(8-hydroxyquinolinolato) aluminum"; Chen, et al.; *Applied Physics Letters*; vol. 75, No. 25, Dec. 20, 1999, pp. 4010-4012.
"Influence of the hole transport layer on the performance of organic light-emitting diodes"; Giebeler, et al.; *Journal of Applied Physics*; vol. 85, No. 1, Jan. 1, 1999, pp. 608-615.
"Diphenylthienylamine-Based Star-Shaped Molecules for Electroluminescence Applications"; Wu, et al.; *Chem. Mater.*; 2001, 13, 2626-2631.
"Starburst Molecules Based on Hexathienylbenzene Units: Potential Hole-Transport Materials"; Wu, et al.; *Adv. Mater.*; 2000, 12, No. 9, pp. 668-669.
"Influence of hole transporting material on device performance in organic light-emitting diode"; Tokito, et al.; *Thin Solid Films*; 363 (2000) 290-293.
"The electroluminescence of organic materials"; Mitschke, et al.; *J. Mater. Chem.*; 2000, 10, 1471-1507.
"Characterization of Hole Transport in a New Class of Spiro-Linked Oligotriphenylamine Compounds"; Bach, et al.; *Adv. Mater.*; 12, No. 14, Jul. 19, 2000, pp. 1060-1063.
"Low molecular organic glasses for blue electroluminescence"; Salbeck, et al.; *Synthetic Materials*; 91 (1997) 209-215.
"EL properties of organic light-emitting-diode using TPD derivatives with diphenylstylyl groups as hole transport layer"; Yamashita, et al.; *Thin Solid Films*; 363 (2000) 33-36.
"Organic electroluminescent diodes"; Tang, et al.; *Appl. Phys. Lett.*; 51 (12), Sep. 21, 1987, pp. 913-915.
"Thermally stable organic light-emitting diodes using new families of hole-transporting amorphous molecular materials"; Shirota, et al.; *Synthetic Metals*; 111-112 (2000) 387-391.

* cited by examiner

Primary Examiner—Marie Yamnitzky
(74) Attorney, Agent, or Firm—Dickstein, Shapiro, LLP.

(57) ABSTRACT

Materials containing one or more borazine rings are employed as materials for electroluminescent devices. The compounds have molecular structures represented by the following formula:

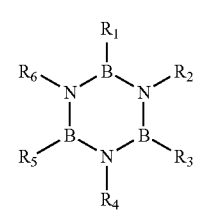

in which $R_1$–$R_6$ are independently a metal; a whole or part of an optionally substituted borazine ring; hydrogen; halogen; hydroxyl; optionally substituted alkyl, cycloalkyl, aryl, acyl, alkoxy, acyloxy, amino, acylamino, aralkyl, cyano, carboxyl, thio, vinyl, styryl, aminocarbonyl, carbamoyl, aryloxycarbonyl, phenoxycarbonyl, or alkoxycarbonyl, as well as recognized donor and acceptor groups. The compounds have high thermal stability as well as hole and electron mobilities.

19 Claims, 6 Drawing Sheets

MATERIALS FOR ELECTROLUMINESCENT DEVICES

FIELD OF THE INVENTION

The present invention relates to novel electroluminescent (EL) devices, including organic and polymer light-emitting devices (OLEDs and PLEDs), which are capable of emitting light in the UV or the visible regions. More particularly, this invention relates to the employment of borazine-containing materials in one or more layers of EL devices, OLEDs and PLEDs. Such layers include the hole-injection layer, hole-transporting layer, electron-injection layer, electron-transporting layer, emissive layer comprising of a single emitter or host with one or more emissive dopant(s) hole-blocking layer and/or electron-blocking layer and the like, but are not limited to these examples. The application of the aforesaid materials in EL devices can enhance the device performance, including but not limited to, the achievement of purer color, higher efficiency and lower driving voltage. Further, the present invention relates to the processes for effectively preparing the materials.

BACKGROUND OF THE INVENTION

Organic electroluminescence was first observed and studied in 1960's (E. Gurnee et al., U.S. Pat. No. 3,172,862 (1965)). In the 1980's, an optimized double-layer structure for an OLED, which employed organic thin films prepared by vapor deposition, was invented (C. W. Tang, U.S. Pat. No. 4,356,429 (1982); C. W. Tang et al., *Appl. Phys. Lett.* 51, 12: 913 (1987)). A conducting polymer-based OLED or PLED was announced shortly after that (R. Friend et al., WO Patent 90/13148 (1990); R. Friend et al., U.S. Pat. No. 5,247,190 (1993)). Since then, there has been growing interest in the research and development of OLED; the growing interest is mainly motivated by the promise of OLED's use in flat panel display technology.

An OLED is comprised of an organic electroluminescent medium, with thickness of the order of 100 nanometers, sandwiched between two electrodes. The most commonly used device configurations of OLED and PLED nowadays can be generally categorized into three types: single layer, double layer and multilayer. Single layer devices, which are the easiest to manufacture among the three, have only a single electroluminescent layer between the anode and the cathode. In a double layer structure, the two layers are responsible for transporting holes and electrons, respectively. One of the hole-transporting or electron-transporting layers is also the emitting layer. In a multilayer device, an emitting layer is inserted between the hole-transporting and the electron-transporting layers; other layers such as hole-blocking, electron-blocking or layers acting as "steps" to its adjacent layer may also be present.

To improve device performance, novel device configurations and materials for OLED and PLED have continuously been investigated. Therefore, there have been many more new device structures other than the three general configurations named above. However, one of the factors that limits the lowering of the driving voltage and enhancement of efficiency is charge transport (L. S. Hung et al., *Mater. Sci. Eng. R.* 39: 143 (2002)). Emission from non-targeted species present in the device, especially the host, is another obstacle to overcome before high color purity can be obtained; and full color displays can only be achieved when the colors can be controlled under varying currents. Therefore, the search for non-emitting (in the visible region) materials with high charge mobilities, especially for use in the charge transporting layers and hosts for emitting dopants, has become one of the hottest topics for OLED nowadays.

By far, one of the most widely used hole-transporting material (hereinafter referred to as HTM) in OLED is 4,4'-bis[N-(1-naphthyl)-N-phenylamino]biphenyl (hereinafter referred to as NPB, S. A. VanSlyke et al. U.S. Pat. No. 5,061,569 (1991)). Although the glass transition temperature ($T_g$) of NPB at 98° C. is rather low, it is still popular due to the ease of manufacturing. Hence, the search on new HTM has been focused on those materials with high thermal stabilities along with high charge mobilities (L. S. Hung et al., *Mater. Sci. Eng. R.* 39: 143 (2002)). These approaches to HTM are mainly focused on biphenyl diamine derivatives (Y. Shirota et al., *Synth. Met.* 111:387 (2000); D. F. O'Brien et al., *Adv. Mater.* 10, 14: 1108 (1998); K. Yamashita et al., *Thin Solid Films,* 363:33 (2000)), spiro-linked biphenyl amines (J. Salbeck et al., *Synth. Met.* 91:209 (1997); U. Bach et al., *Adv. Mater.* 12: 1060 (2000); U. Mitschke, *J. Mater. Chem.* 10: 1471 (2000); S. Tokito et al., *Thin Solid Films,* 363: 290 (2000)), and starburst amorphous materials (Y. Shirota et al., *Synth. Met.* 111: 387 (2000); I.-Y. Wu et al., *Adv. Mater.* 12: 668 (2000); I.-Y. Wu et al., *Chem. Mater.* 13: 2626 (2001); C. Giebeler et al., *J. Appl. Phys.* 85: 608 (1999)).

The most widely used electron-transporting material (hereinafter referred to as ETM) and/or host material in OLED is 8-hydroxyquinoline aluminum (hereinafter referred to as $Alq_3$, C. W. Tang et al., *Appl. Phys. Lett.* 51, 12: 913 (1987); B. J. Chen et al., *Appl. Phys. Lett.* 75, 25: 4010 (1999); R. G. Kepler et al., *Appl. Phys. Lett.* 66, 26: 3618 (1995)). The popularity comes from its thermal and morphological stability, ease of synthesis, purification and deposition into thin films. It is also molecularly shaped to avoid exciplex formation (L. S. Hung et al., *Mater. Sci. Eng. R.* 39: 143 (2002)). $Alq_3$ is, however, green fluorescent and requires the use of a hole-blocker (Y. Hamada et al., *Jpn. J. Appl. Phys.* 40: L753 (2001)) when the emission from another material is desired. Moreover, no blue emission can be obtained from any fluorescent or phosphorescent emitter when $Alq_3$ is used as the host since it is impossible to emit light with energy higher than the band gap of $Alq_3$.

Therefore, the present inventors made extensive investigations to develop a new class of multifunctional and thermally stable compounds with high hole and electron mobilities for use in the different layers of an OLED. They have found that materials based on an inorganic analog of benzene, namely borazine or borazole, can be used. A number of derivatives of borazine are known for other purposes. For example, a low dielectric film based on borazine materials is described in U.S. Pat. No. 6,458,719.

SUMMARY OF THE INVENTION

The present invention provides multifunctional materials with high hole and electron mobilities and thermal stability which can be used in one or more layers of an EL device, including an OLED or PLED. The materials of this invention are represented by formula I,

I which includes the skeleton of a borazine ring, that is a six-membered ring with alternating B and N; and wherein $R_1$–$R_6$ are each independently selected from the group consisting of metal; the whole or part of a borazine ring or substituted borazine ring; hydrogen; halogen; hydroxyl; unsubstituted or substituted alkyl group, cycloalkyl group, aryl group, acyl group, alkoxy group, acyloxy group, amino group, acylamino group, aralkyl group, cyano group, carboxyl group, thio group, vinyl group, styryl group, aminocarbonyl group, carbamoyl group, aryloxycarbonyl group, phenoxycarbonyl group, and alkoxycarbonyl group, with the substituents selected from metals, hydrogen, halogens, and hydroxyl groups as well as recognized donor and acceptor groups; wherein the substituents, for example, on the aryl group, may combine together to form a substituted or unsubstituted, saturated or unsaturated ring with any number of members, which may contain heteroatoms. Further, $R_1$ to $R_6$ can be the same or different in formula I. Preferably, at least one of the substitutents on the borazine ring are or contain an aromatic ring. These materials include both known and novel compounds.

The invention also provides an EL device of enhanced performance, including but not limited to, purer color achievement, higher efficiency and lower driving voltage. Therefore, this invention is also directed to the application of the aforesaid materials in EL devices, in particular OLEDs and PLEDs. The employment of these materials can be in any, or one or more of the following layers of the devices: hole-injection layer, hole-transporting layer, electron-injection layer, electron-transporting layer, emissive layer comprising of a single emitter or host for one or more emissive dopant(s), hole-blocking layer and/or electron-blocking layer, and the like, but is not limited to the above examples. In the devices, thin films of the materials based on formula I alone or the materials based on formula I doped with other materials for use in EL devices including OLEDs and PLEDs are made with vapor deposition, spin-coating, inkjet printing processes and the like, but are not limited to these examples. These devices are capable of emitting light in the UV or visible regions. With the high thermal stability as well as hole and electron mobilities of the aforesaid materials, the application of these materials in EL devices is proven to enhance the device performance, such as increasing the efficiency and lowering the driving voltage. In particular, when the materials based on formula I, which do not emit in the visible region, is used as a host for the emitter, unwanted emission from non-target species would be absent and the color of the device can hence be controlled under varying currents.

The present invention is also directed to the effective preparation processes of the materials based on formula I.

DETAILED DESCRIPTION OF THE INVENTION

The present invention provides multifunctional materials with high hole and electron mobilities and thermal stabilities to be used in one or more layers of EL devices, including OLEDs and PLEDs. The materials of this invention are represented by formula I, wherein $R_1$–$R_6$ are each independently selected from the group consisting of:
  a metal, such as Ru, Os, Co, Rh, Ir, Ni, Pd, Pt, Cu, Ag, Au and the like, but is not limited to the above examples;
  a whole or part of a borazine ring or substituted borazine ring;
  a hydrogen;
  a halogen, i.e., F, Cl, Br, and I;
  a hydroxyl group;

as well as unsubstituted or substituted groups of:
  an alkyl group, such as methyl, ethyl, propyl, butyl and the like, but not limited to the above examples;
  a cycloalkyl group, such as cyclohexyl and the like, but not limited to the above example;
  an aryl group, such as phenyl, naphthyl, anthrayl, diphenyl and the like, but not limited to the above examples;
  an acyl group such as formyl, acetyl, propionyl or butylyl and the like, but not limited to the above examples;
  an alkoxy group, such as methoxy, ethoxy, propoxy, butoxy and the like, but not limited to the above examples;
  an acyloxy group such as acetyloxy, propionyloxy or butylyloxy and the like, but not limited to the above examples;
  an amino group;
  an acylamino group such as acetylamino, propionylamino, butylylamino and the like, but not limited to the above examples;
  an aralkyl group, such as benzyl, phenoxy, tolyloxy and the like, but not limited to the above examples;
  a cyano group;
  a carboxyl group;
  a thio group;
  a vinyl group;
  a styryl group;
  an aminocarbonyl group, such as anilinocarbonyl and the like, but not limited to the above example;
  a carbamoyl group;
  an aryloxycarbonyl group; such as naphthyloxycarbonyl and the like, but not limited to the above example;
  a phenoxycarbonyl group;
  an alkoxycarbonyl group, such as methoxycarbonyl, ethoxycarbonyl or butoxycarbonyl and the like, but not limited to the above examples;

with the substituents being the listed above metals, hydrogen, halogens and hydroxyl groups, as well as recognized donor and acceptor groups;

wherein the substituents, for example, on an aryl group, may combine together to form a substituted or unsubstituted, saturated or unsaturated ring with any number of members.

Further, $R_1$ to $R_6$ can be the same or different in formula I.

Representative examples of the materials based on formula I are shown below. The present invention is, however, not limited to these shown examples.

Compound 1

Compound 2

Compound 3

Compound 4

Compound 5

Compound 6

Compound 7

Compound 8

-continued

Compound 9

Compound 10

Compound 11

In preferred embodiments, there are three general methods for effectively preparing the materials in the representative examples, that for the B-substituted, N-substituted and B, N-substituted materials. Preparation of these materials, however, is not limited to these three examples.

In preferred embodiments, N,N',N"-trisubstituted borazines or 1,3,5-trisubstituted borazines (where the substituted group is denoted by R) are prepared based on modification of the procedure described in M. P. Brown et al., GB Patent 1050434 (1966). The appropriate substituted aniline compound, R—NH$_2$ (0.05 mol), is introduced into a round-bottom flask containing borane triethylamine compound (0.06 mol) under an argon atmosphere. The mixture is heated to 80° C. for 16 hours, and then further to 180° C. Afterwards, the excess reactant is removed in vacuo. The product is collected upon cooling the reaction mixture to room temperature, and then purified using high vacuum sublimation.

In preferred embodiments, B,B',B"n-trisubstituted borazines or 2,4,6-trisubstituted borazines (where the substituted group is denoted by R) are prepared based on modification of the procedures described in E. F. Rothgery et al. *Inorg. Chem.* 6, 5: 1065 (1967) and K. Niedenzu et al., *J. Am. Chem. Soc.* 81: 3561 (1959). The appropriate R$_2$—NH$_2$ (0.03 mol) is introduced into a round-bottom flask containing 40 mL calcium chloride-dried chlorobenzene under an argon atmosphere. Boron trichloride gas is then continuously bubbled into the solution until fuming is observed above the flask neck, indicating that all acetronitrile is consumed. Dried ammonium chloride powder (2.8 g) is added and the reaction mixture is refluxed for 3 hours. Upon cooling the reaction mixture to room temperature, the chlorobenzene is removed using a cannula. This is followed by the introduction of 150 mL benzene into the reaction mass, and after that the addition of 100 mL a benzene solution of the appropriate R—H (0.09 mol) dropwise to the reaction mixture. The reaction mixture is then refluxed for 16 hours. The product is collected with filtration and purified using high vacuum sublimation.

In preferred embodiments, B,B',B"—R$_1$—N,N',N"—R$_2$ substituted borazines or 1,3,5-R$_1$-2,4,6,—R$_2$ substituted borazines (where the substituted group is denoted by R$_1$ and R$_2$) are prepared based on modification of the procedures described in S. J. Groszos et al., *J. Am. Chem. Soc.* 80: 1357 (1958) and K. Niedenzu et al., *J. Am. Chem. Soc.* 81: 3561 (1959). The appropriate R$_2$—NH$_2$ (0.03 mol) is introduced into a round-bottom flask containing 100 mL of freshly distilled toluene under an argon atmosphere. Boron trichloride gas is then continuously bubbled into the solution until fuming is observed above the flask neck. The reaction mixture is refluxed overnight. Upon cooling the reaction mixture to room temperature, the solution is removed using a cannula. This is followed by the introduction of 150 mL benzene into the reaction mass, and after that the addition of 100 mL a benzene solution of the appropriate R$_1$—H (0.09 mol) dropwise to the reaction mixture. The reaction mixture is then refluxed for 16 hours. The product is collected with filtration and purified using high vacuum sublimation.

To provide EL devices of enhanced performance, including but not limited to high color purity, efficiency and low driving voltage, the materials based on formula I are employed in EL devices, in particular OLEDs.

In preferred embodiments, the materials based on formula I have substituents R$_1$=R$_3$=R$_5$=phenyl group and R$_2$=R$_4$=R$_6$=H (2,4,6-triphenylborazine, Compound 1); or R$_1$=R$_3$=R$_5$=H and R$_2$=R$_4$=R$_6$=phenyl group (1,3,5-triphenylborazine, Compound 2); or R$_1$=R$_3$=R$_5$=diphenylamino group and R$_2$=R$_4$=R$_6$=H (2,4,6-tris(diphenylamino)borazine, Compound 3) to give conjugated structures. The aforesaid materials are thermally stable and possess high hole and electron mobilities. The highest occupied molecular orbitals (hereinafter referred to as HOMO) are at a position that is suitable to be used in the hole-transporting layer of an OLED. Although, the lowest unoccupied molecular orbitals (hereinafter referred to as LUMO) may be at relatively high energies, the high electron mobilities of these compounds make them useful as the ETM even though a "step" may be required next to the cathode for the enhancement of electron injection. On the other hand, the high LUMO also makes these materials usable as electron-blocking materials (hereinafter refer to as EBM). Since the LUMO is high, the band gap for the foresaid materials is typically large. The absorption and emission of these materials are in the UV region thereby making the materials good hosts for emitting dopants. Since these materials have no emission in the visible region, they will not affect the color purity of the target emitting dopant(s). For example, $Alq_3$ is often used as a host for the red-emitting devices; however, such a device with good color purity would be hard to achieve due to the emission of $Alq_3$. When the dopant concentration is increased, the color purity would be enhanced. Nevertheless, this results in a device with lower efficiency and higher operating voltage (C. H. Chen et al., *Macromol. Symp.* 125: 49 (1997)). Another good use for the materials base on formula I is as the host for blue emitters. Since the choice of the host for blue emitters is very limited, many researchers use blue-emitting materials, such as TPBI (2,2',2"-(1,3,5-benzenetriyl)tris[1-phenyl-1H-benzimidazole], also known as 1,3,5-tris (N-phenylbenzimidazol-2-yl)benzene) as the host, and end up having difficulty resolving the emission of the dopant from that of the host when the spectra are very close. Further, with the high hole and electron mobilities, the aforesaid materials are especially suitable for use as hosts for emitting dopants in single layer devices. As these materials are useful in one or more layers of an EL device, they are referred to as multifunctional.

In a preferred embodiment, materials based on formula I with substituents carefully selected from, for example, fluorescent groups such as diphenyl and naphthyl, exhibit emissions that can be red-shifted to the visible region. These materials would therefore be fluorescent or would give photoluminescence and/or electroluminescence in the solid state, and can then be used alone as emitters or as emitting dopants in OLEDs.

The use of these materials can be in any one or more of the following layers of the devices: the hole-transporting layer, hole-injection layer, electron-transporting layer, electron-injection layer, emissive layer comprising of a single emitter or host with one or more emissive dopant(s), hole-blocking and/or electron-blocking layer and the like, but are not limited to the above examples. The devices, thin films of the materials based on formula I alone or the materials based on formula I doped with other materials for use in EL devices including OLEDs and PLEDs, are made with vapor deposition, spin-coating, inkjet printing processes and the like, but are not limited to the above examples. These devices are capable of emitting light in the UV or visible regions. With the high thermal stability as well as hole and electron mobilities of the foresaid materials, the application of these materials in EL devices is proven to enhance the general device performance. In particular, when these materials, which do not emit in the visible region, is used as a host for the emitter, unwanted emission from non-target species would be absent; the color of the device can hence be controlled under varying currents.

In a preferred embodiment, the present invention relates to a double-layer OLED which employs a material based on formula I as the HTM in the hole-transporting layer and gives emission in the visible region at room temperature. The device is comprised of layers of materials in the order of:
  a substrate upon which a first electrode is placed;
  a material based on formula I as the HTM in the hole-transporting layer;
  an emissive layer of a single material which is an ETM, or of a host which is an ETM along with one or more emissive dopants; and
  a second electrode;

wherein this device the materials of the emissive layer can also be material(s) based on formula I. Preferably, $Alq_3$ is used in the emissive layer. This invention is, however, not limited to this preference.

In a preferred embodiment, the present invention relates to an OLED which employs a material based on formula I as the host in the emissive layer and gives emission in the visible region at room temperature. The device is comprised of layers of materials in the order of:
  a substrate upon which a first electrode is placed;
  an emissive layer comprising of a material based on formula I as the host and the HTM along with one or more emissive dopants;
  an ETM in the electron transport layer or a "step" to facilitate efficient electron injection into the emissive layer; and
  a second electrode;

wherein this device, the emissive dopants or the ETM can also be materials based on formula I. Preferably, blue-emitting materials such as perylene are used. Another preference for the emitting material is compounds which contain europium (Eu). This invention is, however, not limited to the above preferences.

In one embodiment, the present invention relates to another OLED which employs a material based on formula I as the ETM in the electron-transporting layer and gives emission in the visible region at room temperature. The device is comprised of layers of materials in the order of:
  a substrate upon which a first electrode is placed;
  a hole-transporting layer;
  an emissive layer comprising of either a single material or a host with one or more emissive dopants;
  an ETM of a material based on formula I in the electron-transporting layer; and
  a second electrode;

wherein this device the HTM in the hole-transporting layer and the material(s) in the emissive layer can also be materials based on formula I.

In one embodiment, the present invention relates to an OLED that employs material(s) based on formula I in the emissive layer and gives emission in the visible region at room temperature. The device is comprised of layers of materials in the order of:
  a substrate upon which a first electrode is placed;
  a hole-transporting layer;
  an emissive layer comprising of either a single material based on formula I or a host with one or more emissive dopants of material(s) based on formula I;
  a electron-transporting layer; and
  a second electrode.

wherein this device the HTM in the hole-transporting layer and, the host in the emissive layer and the ETM in the electron-transporting layer can also be materials based on formula I.

In preferred embodiments, the invention includes, but is not limited to, OLEDs with single layer, double layer or multilayer structures. Each of the layers of these devices may contain one or more materials. Preferably, one or more of the materials based on formula I is/are employed in one or more layers of the devices. Advantageously, OLEDs of the present invention exhibit enhanced performance, including but not limited to, high color purity, efficiency and low driving voltage.

Non-limiting examples of substrates useful for OLED of the present invention are glass and plastic strips. The first electrode, the anode of the present invention can be, but is not limited to indium-tin-oxide (hereinafter referred to as ITO).

The present invention also relates to the use of an EL device of the invention in flat panel display applications, as backlighting, in combination with filters that may be controlled electronically to provide colored light at a specified position, or in solar cells.

The following examples are set forth to aid in an understanding of the inventions, but are not intended to, and should not be interpreted to, limit in any way the invention as set forth in the claims which follow thereafter.

EXAMPLES

Example 1

Preparation of Compound 2

Freshly distilled aniline (5 g, 0.055 mole) was introduced into a round-bottom flask containing borane triethylamine compound (9 mL, 0.061 mole) under an argon atmosphere. The mixture was heated to 80° C. for 16 hours, and then further to 180° C. Afterwards, the excess reactant was removed in vacuo. The product was collected upon cooling the reaction mixture to room temperature, and then purified using high vacuum sublimation. White solid (3 g, 53% yield) was obtained. $^1$H NMR (300 MHz, CDCl$_3$) δ 7.35 (t, J=6.90 Hz, 6H), 7.25–7.18 (m, 9H), 5.00 (bs, 3H) (notes: t=triplet, m=multiplet, b=broad, s=singlet). $^{13}$C NMR (75 MHz, CDCl$_3$,) δ 148.0, 128.8, 125.2, 124.7. FAB-MS(m/z): 309 [M$^+$]. M. P. 167° C. (DSC). T$_g$: 121° C. T$_d$: 203° C.

Example 2

Preparation of Compound 3

Freshly distilled acetonitrile (2 g, 0.048 mole) was introduced into a round-bottom flask containing calcium chloride-dried chlorobenzene under an argon atmosphere. Boron trichloride gas was then continuously bubbled into the solution until fuming is observed above the flask neck, indicating that all acetonitrile was consumed. Dried ammonium chloride powder (2.8 g) was added and the reaction mixture was refluxed for 3 hours. Upon cooling the reaction mixture to room temperature, the chlorobenzene was removed using a cannula. This was followed by the introduction of 150 mL benzene into the reaction mass, and after that the addition of 100 mL a benzene solution of the 15 g (0.088 mole) diphenylamine dropwise to the reaction mixture. The reaction mixture was then refluxed for 16 hours. The white product (4.5 g, 48% yield) was collected with filtration and purified using high vacuum sublimation. FAB-MS(m/z): 582 [M$^+$]. Anal. Calculated for C$_{36}$H$_{33}$B$_3$N$_6$: C, 74.28; H, 5.71; N, 14.44; Found: C, 74.52; H, 5.74; N, 14.22. M. P. 338° C. (DSC). T$_g$: 277° C. T$_d$: 289° C.

Example 3

The physical parameters for Compounds 1, 2 and 3 were determined and are summarized in Table 1.

| Physical Parameters | Compound 1 | Compound 2 | Compound 3 |
|---|---|---|---|
| Hole Mobility (cm$^2$/V · s) | up to 10$^{-4}$ | up to 10$^{-5}$ | up to 10$^{-5}$ |
| Electron Mobility (cm$^2$/V · s) | up to 10$^{-5}$ | up to 10$^{-6}$ | up to 10$^{-5}$ |
| Decomposition Temperature (T$_d$, ° C.) | 227 | 203 | 287 |
| Glass Transition Temperature (T$_g$, ° C.) | 68 | 112 | 278 |
| HOMO (eV) | −5.3 | −5.3 | * |
| LUMO (eV) | −1.0 | −0.8 | * |
| Absorption λ$_{max}$ (nm) in DMF solution | 264 | 231 | * |
| Emission λ$_{max}$ (nm) in DMF solution | 288 | n.o. | * |

\* = no measurement was made.
n.o. = not observed

Example 4

The charge mobilities of illustrative materials corresponding to 2,4,6-triphenylborazine (Compound 1), 1,3,5-triphenylborazine (Compound 2) and 2,4,6-tris(diphenylamino)borazine (Compound 3) were determined.

Figure 1:
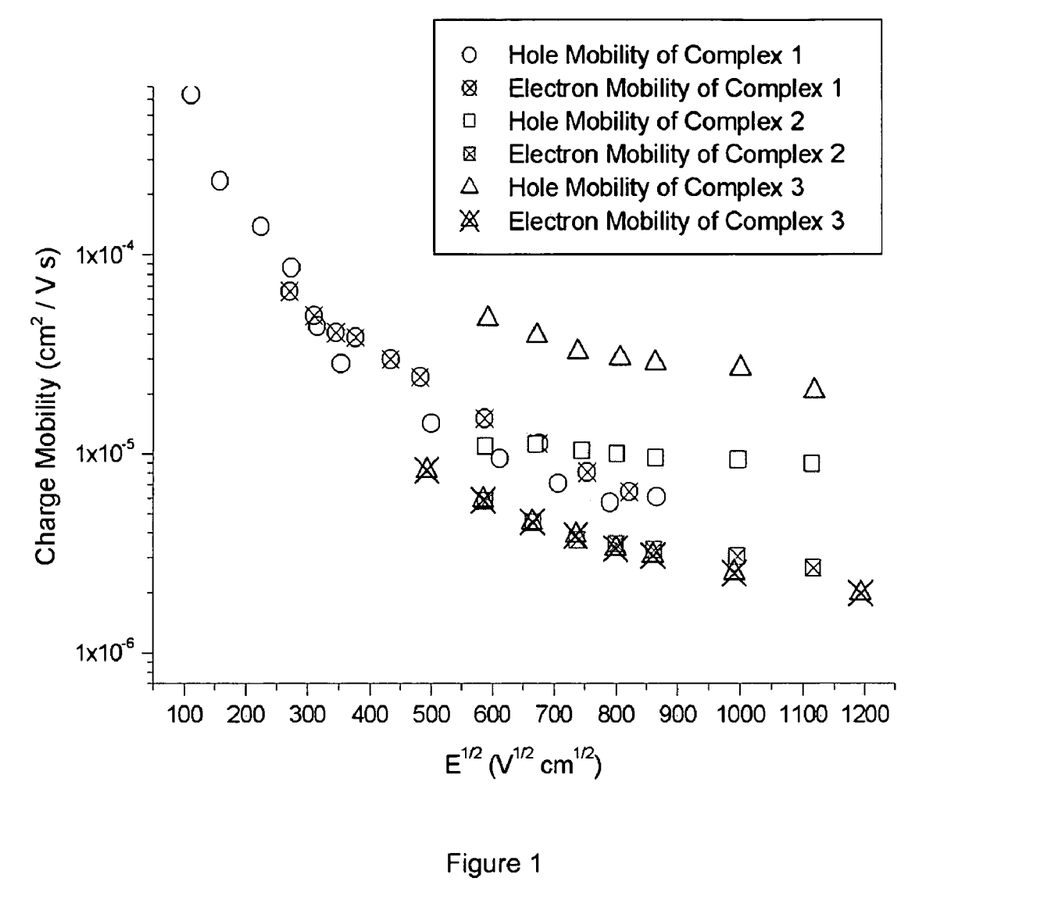
FIG. 1 shows the hole and electron mobilities for illustrative Compounds 1–3 of the present invention at various electric fields.

The hole and electron mobilities of Compounds 1–3 at different electric fields are illustrated in FIG. 1. The three compounds all possess high hole mobility, up to 10$^{-4}$ cm$^2$/V·s, and electron mobility, up to 10$^{-5}$ cm$^2$/V·s (see Table 1). The charge mobilities were measured by the time-of-flight method (hereinafter referred to as TOF, B. J. Chen et al., *Appl. Phys. Lett.* 75, 25: 4010 (1999); B. Chen et al., *Jpn. J Appl. Phys., Part* 1 39, 3A: 1190 (2000)) on thin-film samples sandwiched in the following order: Au (20 nm)/n- or p-type Si/compound (200 nm)/Au (100 nm).

Example 5

The thermal stability of illustrative materials corresponding to Compounds 1–3 were determined.

Figure 2:
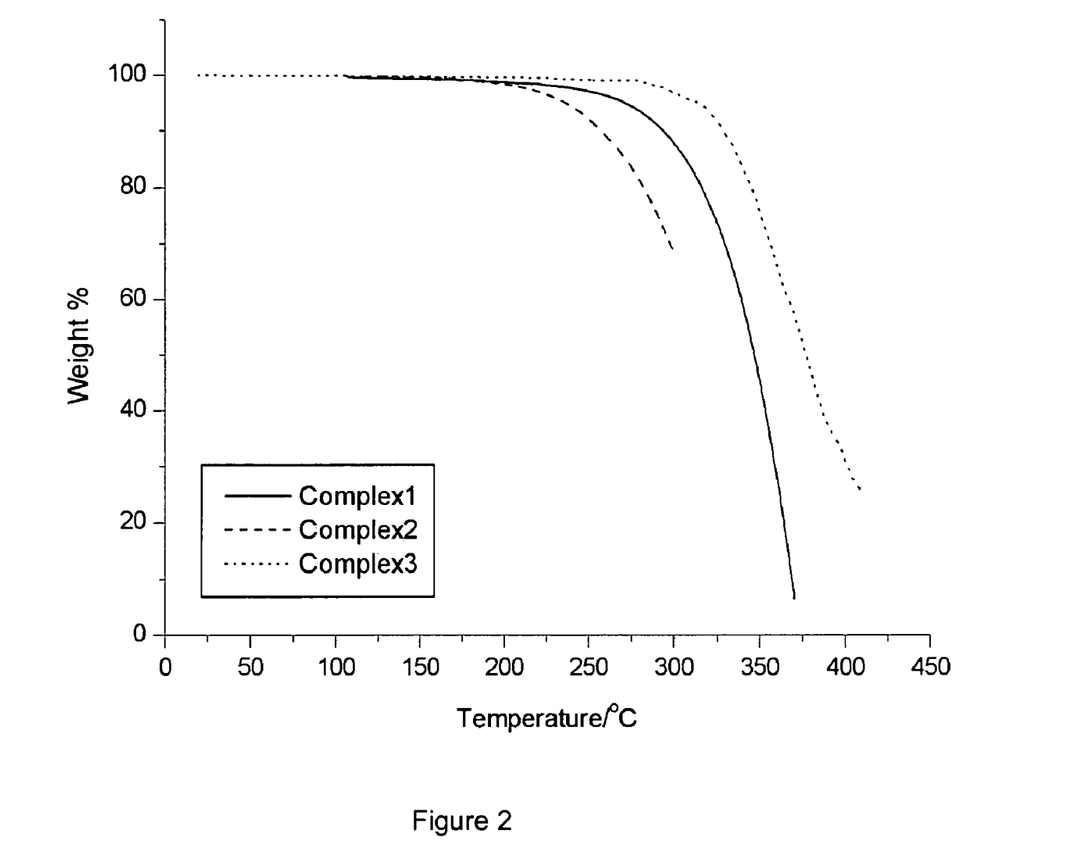
FIG. 2 shows the plots of thermogravimetric analyses (TGA) for illustrative Compounds 1–3.
Figure 3:
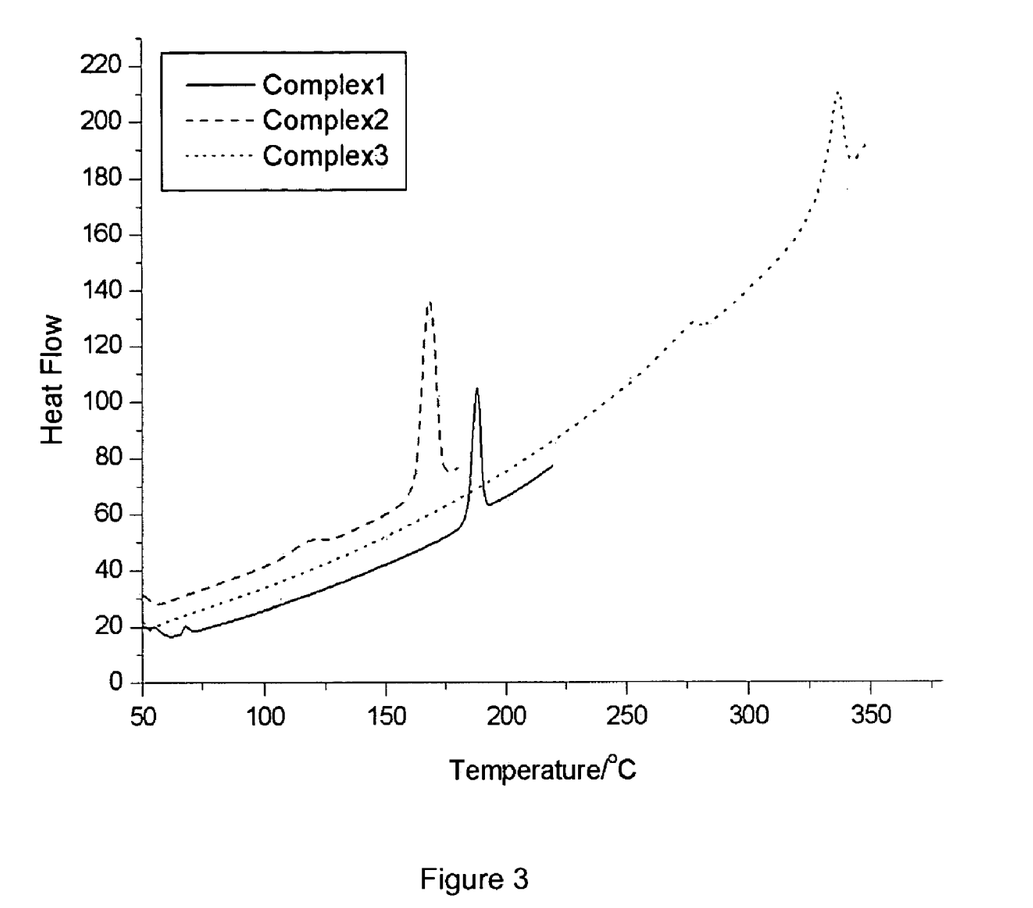
FIG. 3 shows the plots of differential scanning calorimetry (DSC) for illustrative Compounds 1–3.

The thermal behaviors of Compound 1–3 were measured by thermogravimetric analysis (TGA) and differential scanning calorimetry (DSC) at a heating rate of 15° C./min. TGA measures weight changes in a material as a function of temperature or time under a controlled atmosphere, while DSC studies the thermal transitions such as the glass transition by measuring the heat flow. Their principal uses include measurement of a material's thermal stability and composition. The TGA and DSC plots of Compounds 1–3 are shown in FIGS. 2 and 3, respectively. For example, Compounds 1, 2, and 3 are stable up to 227, 203 and 289° C., respectively, under nitrogen atmosphere (see FIG. 2 and Table 1). Meanwhile, the T$_g$ of Compounds 1, 2 and 3 are at 68, 121 and 277° C. (see FIG. 3 and Table 1). Therefore, the three compounds are suitable for sublimation and are stable enough for vacuum deposition as well as for use in EL devices, and would maintain their amorphous nature and refrain from decomposition during operation of the devices.

Example 6

The electrical properties of non-limiting illustrative materials corresponding to Compounds 1 and 2 of the present invention were determined.

Figure 4:
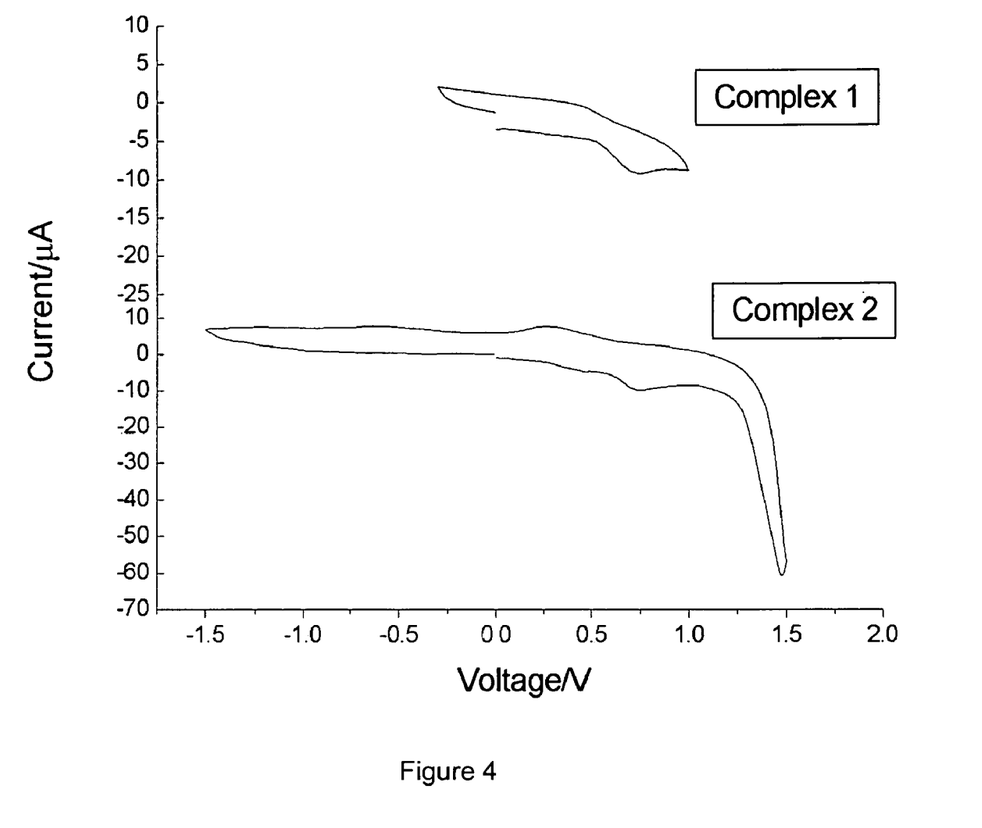
FIG. 4 shows the cyclic voltammograms of illustrative Compounds 1 and 2 in dimethylformamide (DMF) solutions.

The electrochemical properties of Compounds 1–2 were investigated using cyclic voltammetry (CV) on samples dissolved in dimethylformamide (DMF) at a scan rate of 100 mV/s. The potential is continuously changed as a linear function of time, with potential range scanned in one direction and then the direction reversed at the end of the first scan. CV enables the product of the electron transfer reaction that occurred in the forward scan to be probed again in the reverse scan, and allows the determination of redox potentials. The waveforms of Compounds 1 and 2 are shown in FIG. 4. An Ag/AgCl reference electrode was used and the measurements were referenced to the oxidation of ferrocene. The HOMOs for Compounds 1 and 2 are both found to be at around −5.3 eV (see FIG. 4 and Table 1), a position most suited to be used in the hole-transporting layer of an OLED.

Example 7

The absorption and emission properties of materials corresponding to Compounds 1 and 2 of the present invention were determined.

Figure 5A:
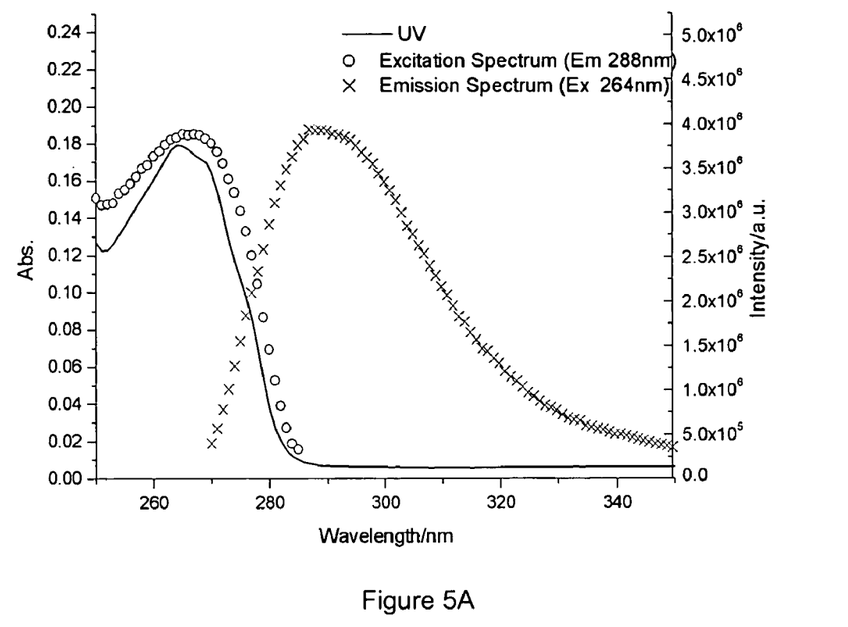
FIG. 5A shows the absorption and emission spectra of illustrative Compound 1 and FIG. 5B, the absorption spectra of illustrative Compound 2 in dichloromethane solutions.
Figure 5B:
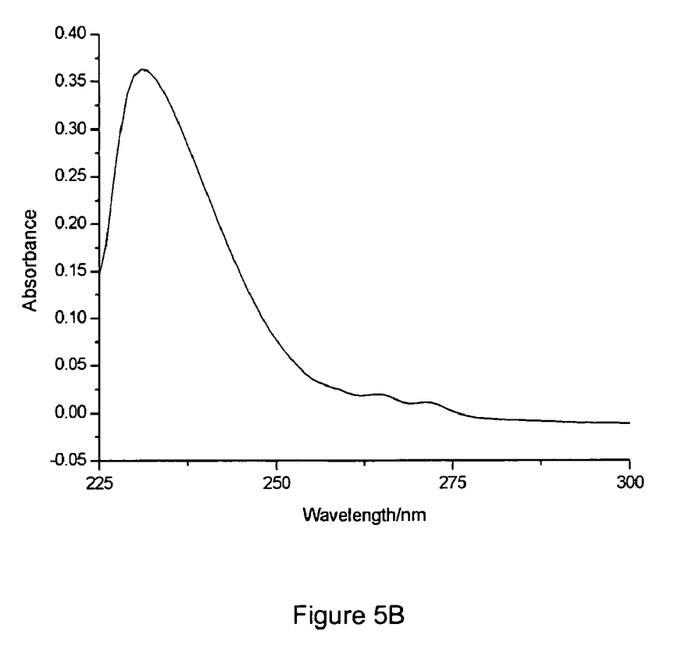

The absorption and emission spectra of compounds 1–2 in dichloromethane solutions are shown in FIGS. 5A and 5B. The two compounds exhibit similar absorption features and possess a low-energy absorption band ($\lambda_{max}$ at 264 and 231 nm respectively, see also Table 1) in the UV-region. The emission for Compound 1 is also in the UV-region ($\lambda_{max}$ at 288 nm for excitation at 264 nm) while there is no emission observed for Compound 2 (see FIG. 5 and Table 1). These results indicate that the two Compounds are good materials, such as being the HTM, ETM or host, for EL device applications, in the sense that the energy of the emitter and thus the light emitted from the device, which is in the visible region, would not be re-absorbed by the compound. Moreover, there would also be no unwanted visible emission from these compounds.

The energy of the LUMOs for Compounds 1 and 2 are calculated from the tail of absorption bands (−1.0 and −0.8 from 289 and 275 nm respectively, see FIG. 5 and Table 1). Although these levels are quite high, the high electron mobility of the two compounds, however, make them useful as the ETM in the electron-transporting layer even though a "step" may be needed next to the cathode to enhance electron injection. On the other hand, the high LUMO also makes these materials usable as electron blocking materials.

Since the LUMO is high, the band gaps for the Compounds 1 and 2 are typically large, at 4.33–4.5 eV. The absorption and emission of these materials are in the high energy UV region; along with their high charge mobilities, these properties make the materials good hosts for emitting dopants.

Example 8

This example describes a non-limiting method for preparing OLED (OLED A) of the present invention. ITO glass with sheet resistance of 20 Ω/square was cleaned first with detergent solution and deionized water, and then three times in sequence with ethanol, toluene, acetone and finally with deionized water. Upon fabrication of the device, the ITO was cleaned using an UV-ozone cleaner. The layers of materials were deposited in sequence on the ITO glass substrate at a rate of 0.2–0.3 nm/s under $5\times10^{-6}$ torr without breaking the vacuum between different deposition processes.

Figure 6:
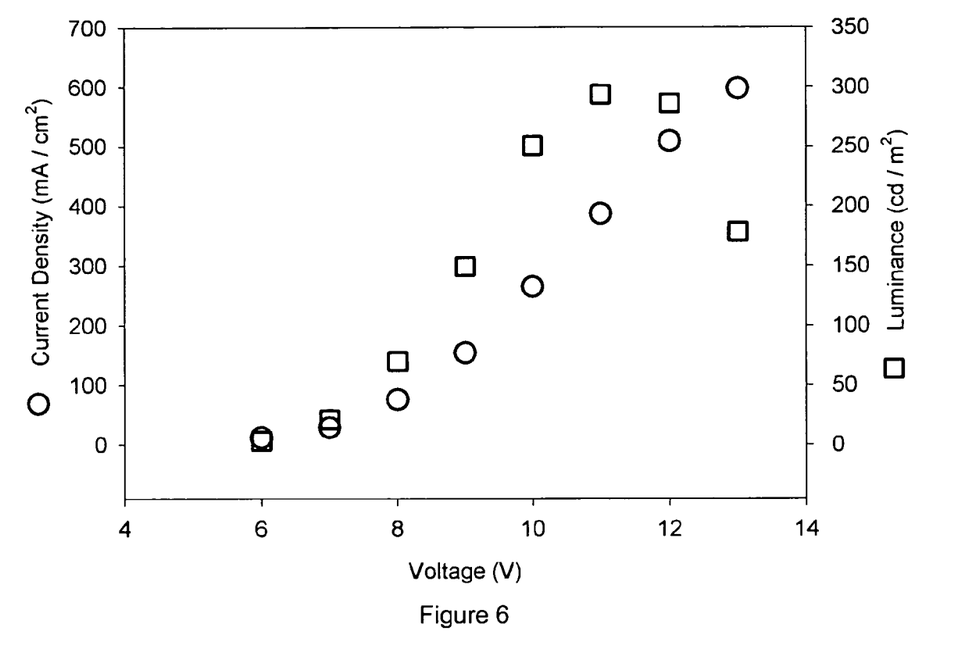
FIG. 6 shows the current density-voltage-luminance curve of illustrative OLED A of the present invention.

The structure of OLED A is ITO/Compound 2 (100 nm)/Alq$_3$ (60 nm)/Mg:Ag (10:1, 250 nm), where Compound 2 acts as the HTM while Alq$_3$ is the ETM. OLED A gives yellow EL emission characteristic of Alq$_3$; the emissive area is 3×3 mm², which is the area where the cathode and the anode overlap. This device exhibits a turn-on voltage of approximately 6V. The maximum efficiency of 1.3 lm/w was achieved at 5V with a luminance of 70 cd/m², and the maximum luminance of 300 cd/m² was obtained at 11V. The current density-voltage luminance characteristics curves of OLED A is shown in FIG. 6.

Various changes and modifications can be made in the process and products of this invention without departing from the spirit and scope thereof. The various embodiments set forth were for the purpose of illustration only and were not intended to limit the invention.

What is claimed is:

1. An electroluminescent device comprising an electroluminescent material sandwiched between electrodes, wherein the electroluminescent material comprises at least one borazine-containing entity represented by formula I, wherein $R_1$–$R_6$ are independently selected from the group consisting of metal; an optionally substituted borazine ring; hydrogen; halogen; hydroxyl; unsubstituted or substituted alkyl group, cycloalkyl group, aryl group, acyl group, alkoxy group, acyloxy group, amino group, acylamino group, aralkyl group, cyano group, carboxyl group, thio group, vinyl group, styryl group, aminocarbonyl group, carbamoyl group, aryloxycarbonyl group, phenoxycarbonyl group, and alkoxycarbonyl group, with the substituents being selected from the group consisting of metals, hydrogen, halogen, hydroxyl, donor groups and acceptor groups; and wherein the substituents together with the group on which they are substituted can form a ring.

2. The electroluminescent device according to claim 1, wherein the $R_1$ to $R_6$ groups of the borazine-containing entity are independently selected from the group consisting of hydrogen, phenyl, diphenyl, diphenylamino, $C_{1-4}$ alkyl, and naphthyl or adjacent groups are linked so as to form a ring.

3. The electroluminescent device according to claim 2, wherein $R_1$, $R_3$ and $R_5$ of the borazine-containing entity are the same and $R_2$, $R_4$ and $R_6$ are the same.

4. The electroluminescent device according to claim 3, wherein one of $R_1$ and $R_2$ of the borazine-containing entity is hydrogen and the other is phenyl or diphenylamino.

5. The electroluminescent device according to claim 3, wherein one of $R_1$ and $R_2$ is methyl and the other is phenyl, diphenyl, diphenylamino or naphthyl.

6. The electroluminescent device according to claim 1, wherein the borazine-containing entity is disposed in at least one layer selected from the group consisting of hole-injection layer, hole-transporting layer, electron-injection layer, electron-transporting layer, emissive layer comprising a single emitter or host with one or more emissive dopant(s), hole-blocking layer and electron-blocking layer.

7. The electroluminescent device according to claim 6, wherein the hole transporting layer comprises the borazine-containing entity.

8. The electroluminescent device according to claim 7, wherein the $R_1$ to $R_6$ groups of the borazine-containing entity are independently selected from the group consisting of hydrogen, phenyl, diphenyl, diphenylamino, $C_{1-4}$ alkyl, and naphthyl or adjacent groups are linked so as to form a ring.

9. The electroluminescent device according to claim 8, wherein $R_1$, $R_3$ and $R_5$ of the borazine-containing entity are the same and $R_2$, $R_4$ and $R_6$ are the same.

10. The electroluminescent device according to claim 9, wherein one of $R_1$ and $R_2$ of the borazine-containing entity is hydrogen and the other is phenyl or diphenylamino.

11. The electroluminescent device according to claim 9, wherein one of $R_1$ and $R_2$ is methyl and the other is phenyl, diphenyl, diphenylamino or naphthyl.

12. The electroluminescent device according to claim 7, wherein $R_1$, $R_3$ and $R_5$ of the borazine-containing entity are the same and are substituted or unsubstituted phenyl and $R_2$, $R_4$ and $R_6$ are hydrogen.

13. The electroluminescent device according to claim 7, wherein the borazine is 1,3,5-triphenylborazine.

14. The electroluminescent device according to claim 1, wherein the device has a single layer between the electrodes.

15. The electroluminescent device according to claim 1, wherein the device has two layers between the electrodes.

16. The electroluminescent device according to claim 1, wherein the device has more than two layers between the electrodes.

17. The electroluminescent device according to claim 1, wherein the electroluminescent material comprises an emitting layer which comprises an emitter and a host therefore in which the host comprises the borazine-containing entity.

18. The electroluminescent device of claim 1 incorporated in a flat panel display.

19. The electroluminescent device of claim 1, wherein the electroluminescent material comprises an emitting layer containing tris(8-hydroxyquinoline) aluminum or 1,3,5-tris(N-phenylbenzimidazol-2-yl)benzene).

* * * * *